United States Patent [19]

Kobayashi et al.

[11] Patent Number: 5,449,625
[45] Date of Patent: Sep. 12, 1995

[54] OPTICAL FIBER BASED FLUORESCENT IMMUNOASSAY APPARATUS

[75] Inventors: Takeshi Kobayashi; Shinji Iijima, both of Nagoya; Yasunori Sakai; Ken-ichi Shimada, both of Gifu, all of Japan

[73] Assignee: Ibiden Co., Ltd., Gifu, Japan

[21] Appl. No.: 98,394

[22] PCT Filed: Dec. 17, 1992

[86] PCT No.: PCT/JP92/01652
§ 371 Date: Aug. 16, 1993
§ 102(e) Date: Aug. 16, 1993

[87] PCT Pub. No.: WO93/13418
PCT Pub. Date: Jul. 8, 1993

[30] Foreign Application Priority Data

Dec. 20, 1991 [JP] Japan .................... 3-356001
May 26, 1992 [JP] Japan .................... 4-160234

[51] Int. Cl.⁶ ............................................ G01N 33/543
[52] U.S. Cl. ....................................... 436/518; 436/527; 436/531; 436/800; 436/807; 435/968; 435/969; 422/82.05; 422/82.06; 422/82.07; 356/417; 250/341.1
[58] Field of Search ............... 436/518, 527, 531, 807, 436/800; 435/968, 969; 422/82.05–82.07; 356/417; 250/341, 361 C

[56] References Cited

U.S. PATENT DOCUMENTS

| | | | |
|---|---|---|---|
| 4,558,014 | 12/1985 | Hirschfield et al. | 436/527 |
| 4,582,809 | 4/1986 | Block et al. | 436/527 |
| 4,666,862 | 5/1987 | Chan | 436/501 |
| 4,716,121 | 12/1987 | Block et al. | 436/514 |
| 4,818,710 | 4/1989 | Sutherland et al. | 436/527 |
| 4,925,268 | 5/1990 | Iyer et al. | 350/96.29 |
| 4,980,278 | 12/1990 | Yamada et al. | 422/82.07 X |
| 5,019,350 | 5/1991 | Rhum et al. | 422/82.07 |
| 5,117,480 | 5/1992 | Yamamoto et al. | 385/145 |

FOREIGN PATENT DOCUMENTS 3-46564 2/1991 Japan .
WO8603004 5/1986 WIPO .

OTHER PUBLICATIONS

L. Jiang et al. "Development of a New Optical FIber Epi-Fluorescence Biosenior System" in SPIE vol. 1648 (1992) pp. 212–222.

M. Sepaniak et al. "Design Considerations for Antibody Based Fiber-Optic Chemical Sensors," Analytical Chemistry, Chemical Sensors and Microinstrumentation (1989) chapter 21, pp. 318–330.

B. Tromberg et al., "Fiber-Optic Chemical Sensors for Competitive Binding Fluoroimmunoassay", Anal. Chem. (1989) vol. 59, pp. 1226–1230.

*Primary Examiner*—Carol A. Spiegel
*Attorney, Agent, or Firm*—Birch, Stewart, Kolasch & Birch

[57] ABSTRACT

The present invention relates to an apparatus for performing a fluoroimmunoassay, the apparatus comprising an excitation light source, a fluorescence detector, an optical fiber for an excitation light from the excitation light source to which an antigen or antibody is bound, and a spectroscope, in which the mentioned antigen or antibody is bound to an outgoing end surface of the optical fiber for the excitation light. In the apparatus the spectroscope is constructed so that it introduces the excitation light emitted from the excitation light source to a incident end surface of the optical fiber for the excitation light and introduces a fluorescence emitted from a fluorescence-labeled antibody or antigen which forms an immunological complex with the antigen or antibody to the fluorescence detector. In the apparatus the outgoing end surface of the optical fiber for the excitation light has a transmittance for the excitation light from the excitation light source. The invention also relates to a sensing chip which is used in the apparatus for performing a fluoroimmunoassay therewith.

7 Claims, 4 Drawing Sheets

OPTICAL FIBER BASED FLUORESCENT IMMUNOASSAY APPARATUS

TECHNICAL FIELD

The present invention relates to an apparatus for performing an immunoassay using a fluoroimmunological reaction, particularly to an apparatus for performing a fluoroimmunoassay using an optical fiber, and to a sensing chip for performing fluoroimmunoassays therewith.

BACKGROUND ART

Traditionally, as methods for measuring the concentrations of an antigen or antibody, methods of labeling an antigen or antibody with a radioisotope or enzyme have been used, but these methods have problems in aspects such as sensitivity and safety; therefore, in place of these methods, various methods of labeling an antigen or antibody with a fluorescent dye, and measuring the concentration of the antigen or antibody therewith have been studied.

For example, Japanese Patent Laid-Open No. 501873/1984 (U.S. Pat. No. 4,582,809) etc., describe a method comprising the steps of binding an antigen or antibody to a side surface of an optical fiber; immunologically reacting an antibody or antigen labeled with a fluorescent dye on this optical fiber surface; an excitation light to the optical fiber, thereby exciting the fluorescent dye on the optical fiber; reflecting this fluorescence on the outgoing end surface of the optical fiber; taking out the fluorescence and residual excitation light from the incident end surface of the optical fiber; spectrally splitting them via a beam splitter; and measuring the fluorescence alone (see instant FIG. 4).

However, in the art described above, when attempts of size reduction, cost reduction and sensitivity improvement for practical application were made, the problems shown below have arisen.

Problems have arisen such as 1) to provide a reflective function, processing for forming a reflector on the tip of the optical fiber is necessary, making the cost high; 2) since a reflective function is provided, excitation light mingles in with fluorescence, and a cutoff filter for cutting excitation light is necessary; 3) when the output-power of the light source is increased for sensitivity improvement, excitation light which cannot be removed with the cutoff filter becomes a background; 4) the optical system is complicated and optical axis adjustment is difficult, thus making it difficult to reduce its size.

As stated above, in the prior art, there has been no immunological analyzer which is safe and which permits size reduction, cost reduction and sensitivity improvement, the same being essential to practical application.

SUMMARY OF THE INVENTION

The present inventors have intensively studied in order to solve the above-mentioned problems, and as a result, they have found that the above-described problems can be solved by binding an antigen or antibody to an outgoing end surface of an optical fiber for the excitation light; and spectrally transmitting the excitation light to the bound antigen or antibody and introducing to a fluorescence detector with a spectroscope a fluorescence emitted from the bound antigen or antibody, spectrally splitting the excitation light to the sample and introducing to a fluorescence detector a fluorescence emitted from the sample with a spectroscope, while at the same time eliminating reflection on the outgoing end surface of the optical fiber (which reflection has conventionally required); and have completed the present invention.

The present invention relates to an apparatus for performing a fluoroimmunoassay, which apparatus comprises an excitation light source, a fluorescence detector, an optical fiber to which an antigen or antibody is bound, and a spectroscope; wherein said antigen or antibody is bound to an outgoing end surface of the optical fiber for the excitation light; wherein said spectroscope is constructed so that it introduces an excitation light emitted from said excitation light source to the incident end surface of said optical fiber for the excitation light and introduces a fluorescence emitted from a fluorescence-labeled antibody or antigen which forms an immunological complex with said antigen or antibody to said fluorescence detector; and wherein an outgoing end surface of said optical fiber for the excitation light has a transmittance for the excitation light from the said excitation light source. The invention further provides for a sensing chip for the apparatus for performing a fluoroimmunoassay therewith, wherein the sensing chip is a portion of the of the optical fiber and contains the outgoing end surface of the optical fiber which has the antigen or antibody bound thereto.

BRIEF DESCRIPTION OF DRAWINGS

FIGS. 1 (a) and (b) are views showing the schematic construction of the apparatus for performing a fluoroimmunoassay of the present invention.

1: light source, 2: detector, 3: optical fiber connector, 4: optical fiber, 5: connection guide, 6: sensing portion (sensing chip), 7: spectroscope, 8: primary antibody, 9: antigen, 10: fluorescence-labeled secondary antibody, 11: spectroscopic unit, 12: fluorescent substance, 13: mirror, 14: half mirror, 15: prism, 16: reference light detector, 17: ratio amplifier, 18: recorder, 19: film which reflects all excitation light and transmits all fluorescence, 20: optical adhesive, 21: film for preventing reflection of fluorescence, 22: excitation light, and 23: fluorescence.

DETAILED DESCRIPTION OF THE INVENTION

The excitation light sources in the present invention generally include semiconductor laser, LED (i.e., light emitting diode), Xe lamp, gas laser, etc., and are not particularly limited thereto, among which the semiconductor laser and LED are preferably used, since they easily permit size reduction and cost reduction.

The fluorescence detectors in the present invention generally include photomultiplier tubes, photodiodes, etc., and are not particularly limited thereto, among which the photodiode is preferably used, since it easily permits size reduction, its strength is great and it is practical.

The optical fiber in the present invention to which an antigen or antibody is bound permits the use of various materials such as glass and resin as the optical fiber, and the optical fiber made of resin is desirable from the viewpoint of cost. As the method for binding an antigen or antibody to the optical fiber, various known methods can be utilized. For example, it is possible to react a silyl compound such as 3,4-aminopropyltrimethoxysilane on a surface of the optical fiber made of glass to introduce an amino group on the surface of the optical fiber and bind thereto the carboxyl group of the antigen or antibody.

Also, in cases where an antigen or antibody is bound to a plastic optical fiber, the optical fiber preferably has an ester structure such as acrylic acid ester polymer, and a compound having a >CH-CHO structure is reacted with this ester group to introduce a formyl group, and the amino group of an antigen or antibody or the like is bound to this formyl group.

The site at which an antigen or antibody is bound to the optical fiber is desirably an outgoing end surface of the optical fiber for the excitation light, since the excitation efficiency becomes high. In cases where an antibody is bound, it may be a monoclonal antibody or a polyclonal antibody.

Figure 1A:
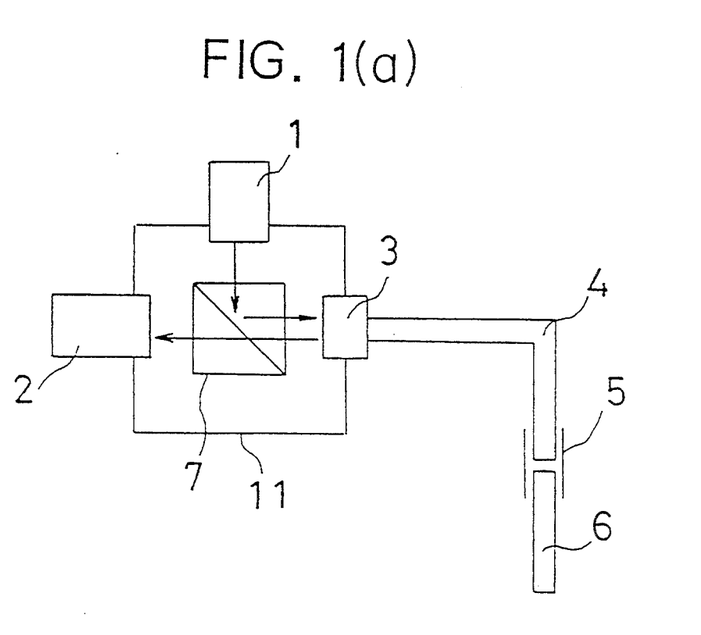
Figure 3:
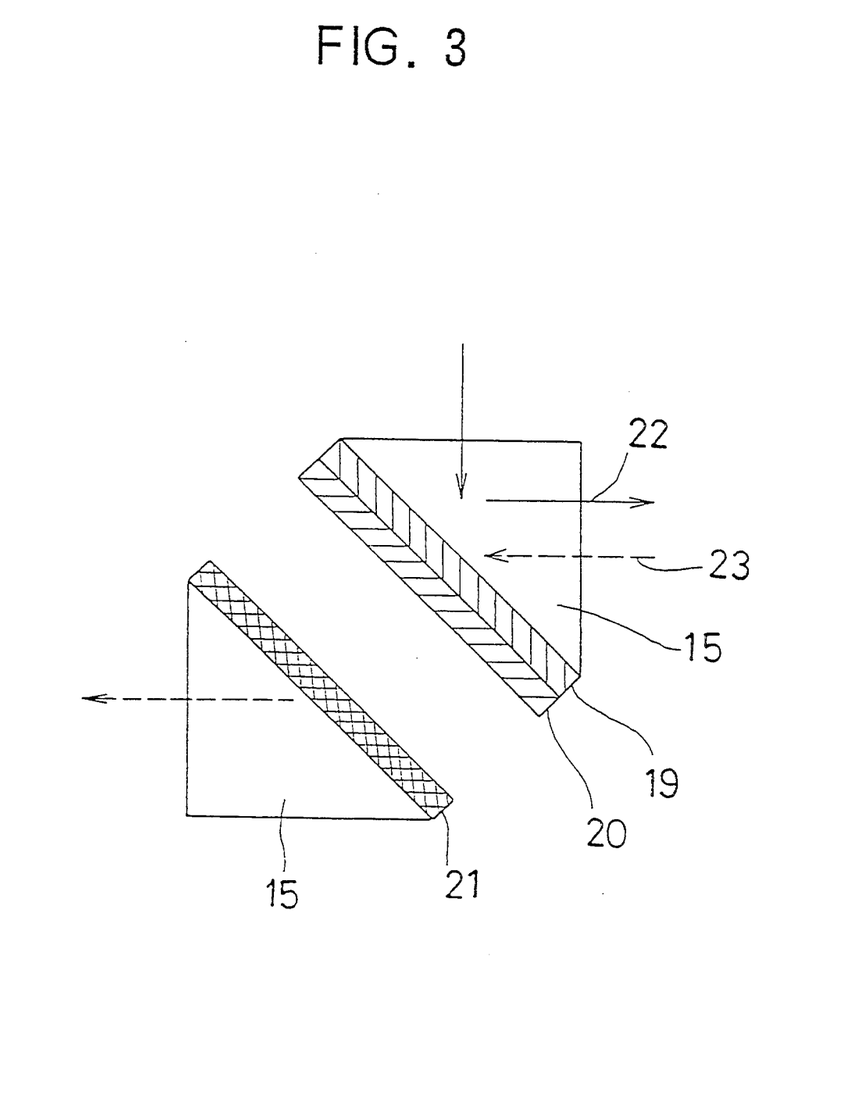
FIG. 3 is a view showing the schematic construction of a spectroscope.

The spectroscope in the present invention is required to be constructed so that it introduces the light emitted from the light source to an incident end surface of the optical fiber for the excitation light to which the antigen or antibody is bound and introduces a fluorescence emitted from a fluorescence-labeled antibody or antigen which forms an immunological complex with said antigen or antibody to a fluorescence detector. The reason for this is that by providing the spectroscope, the excited light incidence to and outgoing from the optical fiber sensing portion can be realized with a single optical system, thereby being suitable for size reduction. The spectroscope in the present invention is not subject to particular limitation, as long as it has such actions. An example includes a combination of a pair of prisms. In this case, in FIG. 1 (a), it is possible to set a film layer 19 which reflects all excitation light and transmits all fluorescence, and a film layer 21 for preventing reflection of fluorescence between a pair of prisms as illustrated in FIG. 3, thereby making it unnecessary to set an excitation light removing filter before the detector 2. The film which transmits all fluorescence or the film for preventing reflection of fluorescence can be prepared using $MgF_2$, MgO, ZnO, $SiO_2$ or $CaF_2$. As a method for forming the film, known methods such as vapor deposition methods can be used.

Figure 1B:
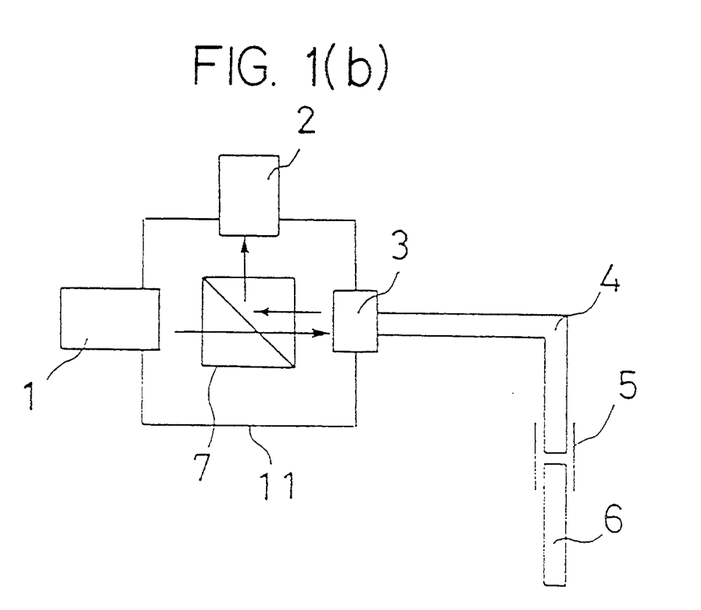

Also, in place of such prisms, a mirror having the characteristics of reflecting all excitation light and transmitting all fluorescence, or a mirror having the characteristics of transmitting all excitation light and reflecting all fluorescence as illustrated in FIG. 1 (b), may be properly prepared and used. As such mirrors, which are not subject to particular limitation, an example includes a dielectric multilayer film mirror. Such a mirror can easily be prepared, for example, by alternately laminating a multiple number of layers of $MgF_2$ and $SiO_2$ on both sides of a glass plate by a vapor deposition method.

The prisms and mirrors described above are spectroscopes utilizing wavelength differences between excitation light and fluorescence, which use prisms having a so-called wavelength selectivity or a dielectric multilayer film mirror having a wavelength selectivity. In cases where a laser having a single polarization plane such as a semiconductor laser is used as an excitation light source, a spectroscope using a dielectric multilayer film mirror having a so-called polarization plane selectivity can also be used.

To describe in detail this spectroscope using a dielectric multilayer film mirror having polarization plane selectivity, in FIG. 1 (a), it is a spectroscope using a dielectric multilayer film having the characteristics of reflecting all light having a particular polarization plane and transmitting light other than the light from the particular polarization plane, which uses a dielectric multilayer film having the characteristics of reflecting all excitation light having a single polarization plane such as a semiconductor laser and transmitting fluorescence other than the light from the particular polarization plane.

In FIG. 1 (b), it is a spectroscope using a dielectric multilayer film having the characteristics of transmitting all light having a particular polarization plane and reflecting light other than the light of the particular polarization plane and, which uses a dielectric multilayer film having the characteristics of transmitting all excitation light having a single polarization plane such a semiconductor laser and reflecting fluorescence other than the light from the particular polarization plane.

To prepare such a mirror, it can easily be obtained, for example, by alternately laminating a multiple number of layers of $MgF_2$ and $SiO_2$ on both sides of a glass plate by a vapor deposition method.

In the present invention, the optical connection between the excitation light source and the spectroscope and the optical connection between the spectroscope and the fluorescence detector can be achieved with an optical fiber. In this case, when a dielectric multilayer film mirror having wavelength selectivity is used, the optical fiber may be of any one; but when a dielectric multilayer film mirror having polarized plane selectivity is used in order to retain the polarization plane, it is required to be a fiber retaining a polarization plane.

Also, it may be that the invention apparatus may be one wherein a light source is irradiated directly to the spectroscope without being mediated by an optical fiber and wherein the generated fluorescence is irradiated directly to the fluorescence detector, and this method apparatus is desirable from the viewpoint of size reduction.

When excitation light from the excitation light source is introduced to the optical fiber to which an antigen or antibody is bound, an optical system such as a lens can be used. But, in the present invention, since a highly sensitive assay is possible, light collection of excitation light with a lens, etc. can be omitted, and the need for optical axis alignment for light collection, which was conventionally necessary, is unnecessary, thereby making the apparatus simple.

In the present invention, an outgoing end surface of the optical fiber for the excitation light to which an antigen or antibody is bound is required to have transmittance for the excitation light from the excitation light source. The reasons therefor are that the excitation light is transmitted, so that the reflection of the excitation light as seen in the prior art can be prevented, and also that the background can be reduced even when the output-power of the excitation light source is increased, so that sensitivity improvement becomes possible.

In the present invention, the outgoing end surface of the optical fiber for the excitation light having transmittance for the excitation light from the excitation light source is of a nature which prevents reflection of excitation light, thereby allowing the excitation light to transmit to such extent that the reflected light which can occur on the outgoing end surface has substantially no influence on fluorescence detection. Specifically, the outgoing end surface of the optical fiber for the excitation light is processed so that in order to provide transmittance with substantially no reflection of the excitation light. More specifically, it is processed so that it possesses a surface roughness characteristic denoted as "Rmax". Rmax is a surface roughness generally of not higher than 5 μm, and Rmax is preferably 0.005 to 5 μm, more preferably 0.01 to 0.5 μm. The reason therefor is that when Rmax exceeds 5 μm, the detection loss of fluorescence becomes greater, or the excitation light undergoes diffused reflection on the outgoing end surface so that the reflected light is likely to be mixed in the fluorescence detector, or the outgoing rate of the light transmitted and discharged from the outgoing end surface lowers. Also, in cases where Rmax is a surface roughness of lower than 0.005 μm, much time is required for processing, and since the surface area becomes smaller, the amount of the antigen or antibody which can be bound decreases so that the sensitivity becomes lower. Rmax which expresses the surface roughness in the present invention is defined in accordance with JIS (Japanese Industrial Standards) B0601.

Accordingly, Rmax is one of indexes for expressing the surface roughness, representing the maximum height. This is referred to as a value expressed in μm obtained by measuring the distance between two straight lines in the direction of the longitudinal magnification of the cross-sectional curve, when the subject surface is cut on a plane at a right angle with respect to the subject surface, and when inserting the portion extracted from a reference length of the cross-sectional curve (the length of the portion extracted from a given length of the cross-sectional curve), which is an outline appearing on the cut surface (hereinafter referred to as extracted portion) between two straight lines in parallel to the average line of the extracted portion.

The method for processing the outgoing end surface of the optical fiber to a surface roughness as described above is not particularly limited, and it can easily be carried out by a conventional method. For example, it is possible to adjust to the desired surface roughness by introducing and fixing the optical fiber to the V-groove portion of a V-groove-worked jig, and a sequential polishing using a water-resistant polishing paper of various surface roughnesses (e.g., #800, #1500, #2000, etc.) and a lapping film. Surface roughness can be measured with instruments for the measurement of surface roughness by a stylus method (manufactured by Tokyo Seimitsusha) in a state in which the optical fiber is fixed to the above-mentioned jig.

Further, the outgoing end surface for the excitation light desirably has an angle θ with respect to the direction of the propagation of incident excitation light. As for the desired angle, it is preferable that θ be as small as possible, since the surface area of the outgoing end surface of the tip end of the optical fiber becomes larger, so that the amount of the antigen or antibody which can be bound to the optical fiber can be increased; however, on the contrary, too small of an angle is undesirable, since the excitation light is likely to be reflected so that the background in turn becomes greater. Therefore, it is desirable that the above-mentioned angle θ of the outgoing end surface of the optical fiber for the incident excitation light with respect to the direction of the propagation of light meet at least the following mathematical formula (1):

$$\theta > (\pi/2) - \sin^{-1}(n2/n1) \qquad (1)$$

(In the formula, θ represents the angle formed between the outgoing end surface and the direction of the propagation of incident excitation light; n1 represents the refractive index of the core portion of the optical fiber; and n2 represents the refractive index of the medium in contact with the optical fiber.)

The immunological complex in the present invention is an antigen-antibody complex forming a sandwich-wise binding of an antibody or antigen used as an assay sample with an antigen or antibody bound to the outgoing end surface of the optical fiber for the excitation light and with an antigen or antibody labeled with a fluorescent dye; or alternatively, it is an antigen-antibody complex forming competitive binding of an antibody or antigen used as an assay sample and an antibody or antigen labeled with a fluorescent dye with an antigen or antibody bound to the outgoing end surface of the optical fiber for the excitation light. Either type of complex is acceptable.

Also, the fluorescent dyes used for fluorescent labeling are not particularly limited, and, for example, cyanine dyes, fluorescein, etc. are used. Also, for the purpose of increasing the fluorescent dye amount, it is possible to use a fluorescence-labeled substance prepared, for example, by a known method (publication of WO90/13029), such as an antibody to which a fluorescent dye is bound via biotin-avidin (antibody-biotin-avidin-fluorescent dye) and that to which a fluorescent dye is bound via chitosan-biotin-avidin (antibody-chitosan-biotin-avidin-fluorescent dye).

In the present invention, it is desirable that the optical fiber for introducing excitation light be separable from the optical fiber to which an antigen or antibody is bound to construct the sensing portion. The reason for this is that the optical fiber, to which an antigen or antibody is bound to construct the sensing portion, is usually disposable, making it easily possible to replace it with a new sensing portion after completion of the assay.

In other words, according to the present invention, a sensing chip for a fluoroimmunoassay is provided wherein an antigen or antibody is bound to the outgoing end surface of the optical fiber for the excitation light. In this sensing chip for a fluoroimmunoassay, the outgoing end surface for the excitation light has transmittance for the excitation light from the excitation light source. The transmittance for excitation light mentioned herein has the same meaning as above, and the outgoing end surface of the optical fiber for the excitation light has a Rmax with a surface roughness of not higher than 5 μm, and it has an angle θ expressed by the above-mentioned mathematical formula (1) with respect to the direction of the propagation of light.

In the present invention, a filter for removing excitation light can be arranged before the detector, but unlike the apparatus of the prior art, there is very little or totally no mixing of the excitation light. Therefore, it is preferable not to arrange a filter, since the loss of fluorescence at the filter is already minimized.

The apparatus for the fluoroimmunoassay of performing present invention comprises an excitation light source, a fluorescence detector, an optical fiber, to which the antigen or antibody is bound, and a spectroscope, wherein the optical fiber to which an antigen or antibody is bound acts as a sensing portion. An immunological reaction is carried out by a so-called sandwich method or a competitive method using a solution of the antigen or antibody used as the assay sample and a solution of an antigen or antibody labeled with a fluorescent dye, thereby forming on the optical fiber an immunological complex comprising an antigen, an antibody and a fluorescent marker (dye). Thereafter, this immunological complex is excited with an excitation light source, and the emitted fluorescence is measured with the fluorescence detector. In the apparatus for performing an fluoroimmunoassay of the present invention, since the reflection of the excitation light in the sensing portion is prevented, there is no mixing of the excitation light with fluorescence, making it possible to improve its sensitivity.

The present invention is hereinafter described in more detail by means of working examples and comparative examples, but the present invention is not limited to these working examples, etc.

EXAMPLE 1

(1) A tip end of a plastic optical fiber of 1 mm in diameter mainly composed of polymethyl methacrylate (produced by Mitsubishi Rayon Co., Ltd., trade name: Esca) was immersed in ethyl acetate, wiped off, and 1 cm of the clad layer was stripped, followed by washing with water. Further, its end surface was cut to an angle of 30° with respect to the direction of the propagation of light, and the cutting surface thereof was polished with polishing paper to adjust the surface roughness so that its Rmax became 0.10 μm. With respect to the optical fiber used in this example, n1 in the above-mentioned mathematical formula (1) was 1.495, and n2 was 1.330.

(2) 10 mg of $NiSO_4$ was dissolved in 0.5 ml of water, and 2.5 ml of ethanol was then added. At this time, since white precipitates were formed, they were centrifuged at 3000 rpm to collect the supernatant, and this was used as an Ni-ethanol solution.

To 0.4 ml of a 50 mM potassium hydroxide-ethanol solution, 0.1 ml of the Ni-ethanol solution and 50 μl of 50% glutaraldehyde were added to give a reaction solution.

(3) The plastic optical fiber in the above (1) was immersed in the reaction solution prepared in the above (2) at 45° C. for 10 minutes, followed by washing with water.

(4) Next, it was immersed in a 20 mM hydrochloric acid solution for 5 to 10 minutes, followed by washing with water to introduce formyl groups onto the surface of the core portion of the plastic optical fiber.

(5) A mouse IgG (antibody 8), which was a monoclonal antibody against Bacillus-derived, heat-resistant α-amylase, was prepared by a conventional method, and 1 mg of the mouse IgG was dissolved in a phosphate-buffered saline (pH=7.5). The plastic optical fiber was immersed in this solution at 4° C. for 12 hours.

Figure 2:
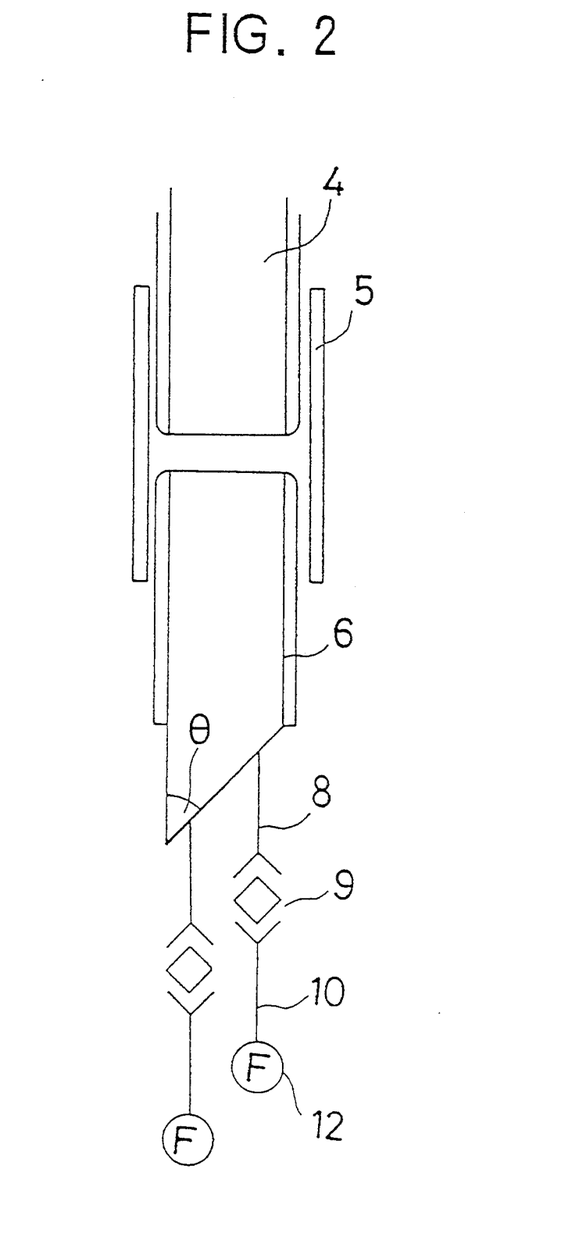
FIG. 2 is a view showing the schematic construction of the sensing portion in the apparatus of the present invention.

(6) The plastic optical fiber was taken out from the solution, washed with water, then immersed in a 1% $NaBH_4$ aqueous solution for 15 minutes, followed by washing with water, thereby immobilizing the mouse IgG (antibody 8) to give a sensing portion 6 (sensing chip) (see FIG. 2).

(7) Next, to one end surface of an optical fiber 4 of the same diameter, a connection guide 5 was attached.

(8) Using a pair of 45° quartz prisms, a film reflecting all excitation light and transmitting all fluorescence such as $MgF_2$ was formed on the slope of the prism on the side of the excitation light source 1 by a vapor deposition method. On the slope of the prism on the side of the detector 2, a film for preventing reflection of fluorescence such as $SiO_2$ was formed by a vapor deposition method, after which this pair of prisms were prepared as a combined type with an optical adhesive to prepare a spectroscope 7 (see FIG. 3).

(9) To the prism of the spectroscope 7 prepared in the above (8), the laser oscillating surface of a semiconductor laser 1 at 650 nm which is an excitation light source, the detector 2, and an end surface of the optical fiber 4 to which the connection guide was not attached were brought into close contact with each other and fixed to the spectroscope unit 11 to make an apparatus for a fluoroimmunoassay (see FIG. 1).

In this assay apparatus, the excitation light emitted from light source unit 1 is guided to the optical fiber 4 via the optical fiber connector 3 by the spectroscope 7 and is guided to the sensing portion 6 whose optical axis has easily been aligned to the optical fiber 4 by the connection guide 5 for the optical fiber, where it excites the fluorescent substance 12 of the fluorescence-labeled secondary antibody 10 shown in FIG. 2, whereby the fluorescent substance 12 generates fluorescence.

This fluorescence is guided to the spectroscope unit via the sensing portion 6, the optical fiber 4 and the optical fiber connector 3, and this fluorescence is introduced to the detector 2 by the spectroscope 7, where fluorescence intensity is measured.

The excitation light which has excited the fluorescent substance 12 does not return to the sensing portion 6, but the fluorescence emitted by the fluorescent substance 12 is introduced to the sensing portion 6 because it has no orientation. For this reason, the background due to the excitation light is low even in the absence of a filter.

(10) 3 mg of $Na_2CO_3$ and 4 mg of biotin were dissolved in 100 μl of water. Next, the above-mentioned solution was added to 2 ml of a 1.8 μM chitosan solution. After adding 100 μl of water, 50 mg of N-cyclohexyl-N'-(2-morpholinoethyl) carbodiimide meto-p-toluenesulfonate (CHMC) was added thereto. Further, while stirring, the reaction was carried out for 5 hours to an overnight at room temperature. 3 Drops of acetic acid was added to terminate the reaction. Next, to the reaction mixture, 4 ml of a mixture solution of 0.3 g/ml $Na_2CO_3$ and 0.3 g/ml NaCl was added to precipitate biotinylated chitosan. After recovering the precipitates using a centrifugal separator, the precipitates were washed with a buffer solution of 0.3 g/ml NaCl and 0.1 g/ml $Na_2CO_3$. The precipitates were dialyzed against 10 ml of 10 mM potassium-phosphate buffer solution (pH=7) for overnight at 4° C. to give a biotinylated chitosan suspension.

(11) To the above-mentioned suspension solution of biotinylated chitosan, a solution of a polyclonal antibody (antibody 10) against the Bacillus-derived heat-resistant α-amylase, which was separately prepared by a conventional method, and CHMC were added, and the mixture was reacted overnight at 4° C. After completion of the reaction, it was dialyzed for 12 hours. Further, unreacted products were removed using an anion exchanging column to yield a biotinylated chitosan, to which the antibody is bound.

(12) 1 mg of avidin and 0.2 ml of triethylamine were dissolved in 1 ml of ethanol. Next, 2 mg of a cyanine dye NK1160 (produced by Japanese Research Institute for Photosensitizing Dyes Co., Ltd.) was added as a fluorescent dye and sufficiently dissolved to prepare a solution. Further, 14 mg of dicyclohexylcarbodiimide (DCC) was added to the above-mentioned solution, followed by a reaction at room temperature for 4 hours. After completion of the reaction, ethanol and triethylamine were removed under reduced pressure by an evaporator. The residue was suspended in 2 ml of a 0.01 M acetate buffer solution (pH=6.5), then centrifuged at 5000 rpm for 10 minutes by using a centrifugal separator to collect the supernatant, and centrifuged again to yield a solution of avidin modified with NK1160.

(13) The sensing portion 6 was immersed in a solution containing Bacillus-derived heat-resistant α-amylase as an assay sample (solution of antigen 9), washed with a solution of physiological saline and immersed in the solution of (11), after which it was immersed in the solution of (12) to bind the fluorescence-labeled secondary antibody 10 to the antigen 9.

(14) Next, the sensing portion 6 was attached to the connection guide 5 and excitation was performed with a semiconductor laser of 3 mW at 650 nm, and fluorescence was measured. The detection sensitivity was $1.2 \times 10^{-4}$ (mg/ml). When the output-power of the semiconductor laser was increased to 30 mW, the detection sensitivity was $0.2 \times 10^{-4}$ (mg/ml), indicating an improvement thereof.

EXAMPLE 2

Fluorescence was measured in the same manner as in Example 1 except that the surface roughness of the outgoing end surface of the excitation light of the optical fiber was adjusted so that Rmax became 0.4 μm in Example 1. The detection sensitivity was $0.3 \times 10^{-4}$ (mg/ml), and good results were obtained.

EXAMPLE 3

Fluorescence was measured in the same manner as in Example 1 except that a dielectric multilayer film mirror having wavelength selectivity formed by laminating three each of alternate layers of $MgF_2$ and $SiO_2$ on a glass plate by the vapor deposition method was used in place of a pair of adhesively combined prisms as the spectroscope 7 in Example 1, and that the antibody 8 to be bound to the outgoing end surface of the optical fiber was replaced with mouse IgG which is a monoclonal antibody against bovine serum albumin (BSA), the antibody 10 was replaced with a polyclonal antibody against BSA, and the antigen 9 was replaced with a BSA solution. The detection sensitivity was $1.0 \times 10^{-5}$ (mg/ml), and good results were obtained.

EXAMPLE 4

Fluorescence was measured in the same manner as in Example 3 except that a dielectric multilayer film mirror having polarization plane selectivity formed by laminating five each of alternate layers of $MgF_2$ and $SiO_2$ on a glass plate by the vapor deposition method was used in place of the dielectric multilayer film mirror having wavelength selectivity as the spectroscope 7 in Example 3. The detection sensitivity was $0.5 \times 10^{-4}$ (mg/ml), and good results were obtained.

COMPARATIVE EXAMPLE 1

Fluorescence was measured in the same manner as in Example 1 except that the surface roughness of the outgoing end surface of the excitation light of the optical fiber was adjusted so that Rmax became 7 μm in Example 1. As a result, the measurement was not possible due to the influence of scattering, reflection and detection loss of fluorescence of the excitation light at the outgoing end surface.

COMPARATIVE EXAMPLE 2

Fluorescence was measured in the same manner as in Example 1 except that the angle θ of the outgoing end surface of the optical fiber for the excitation light was adjusted to 15°. The detection sensitivity was $0.7 \times 10^{-4}$ (mg/ml), indicating the influence of background due to the reflection of the excitation light.

COMPARATIVE EXAMPLE 3

Figure 4:
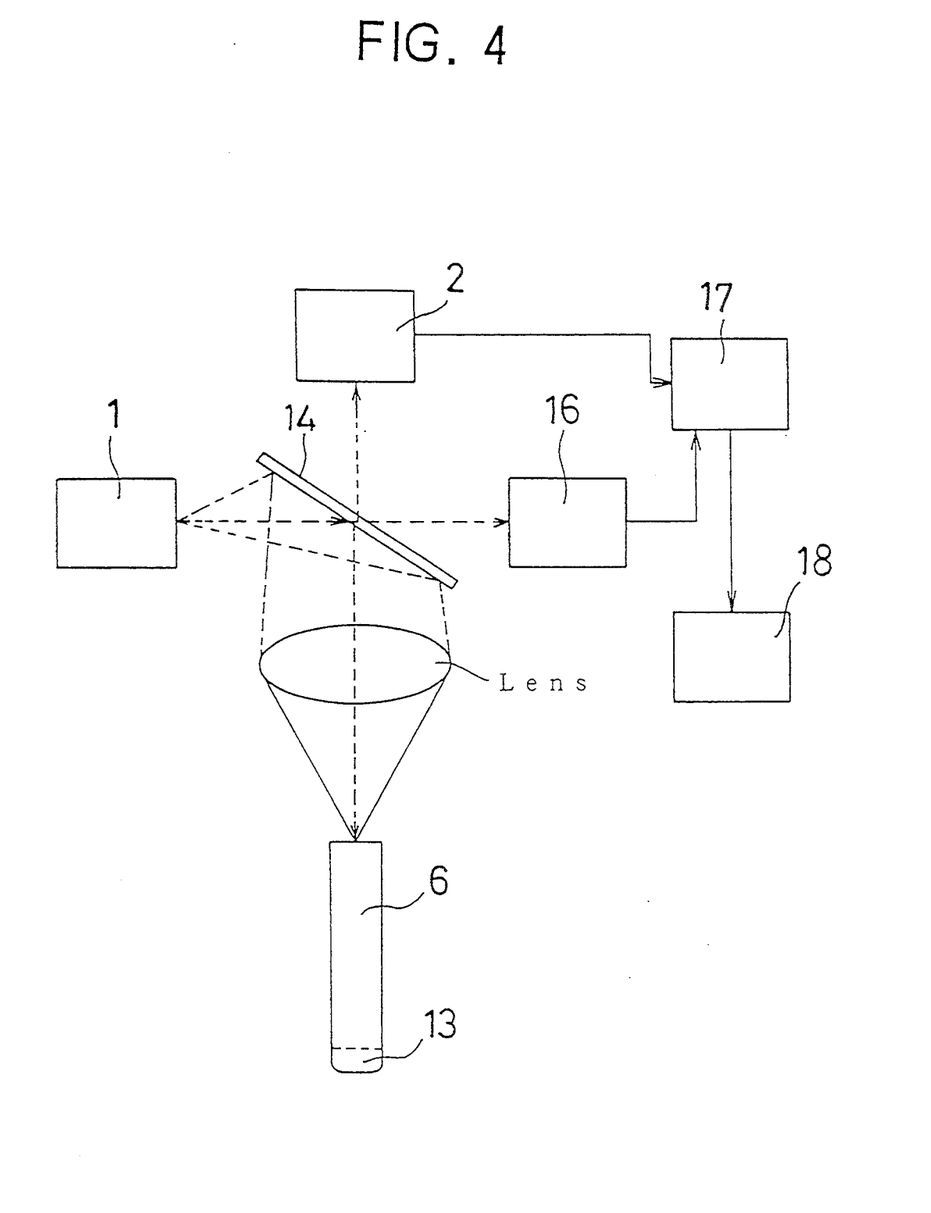
FIG. 4 is a view showing the schematic construction in the apparatus of the prior art. The numerals in each figure are hereinafter described.

Using the apparatus illustrated in FIG. 4, assay was conducted. An optical fiber made of nylon was used, whose surface was hydrolyzed with hydrochloric acid to form an amino group on the surface of the optical fiber, and to this amino group the same antibody 8 as used in Example 1 was bound. Also, to the tip end of the optical fiber, silver was injected by sputtering to form a mirror 13. Also, as a spectroscope, a half mirror 14 was arranged. The subject substance and the assay method are the same as in Example 1.

The excitation was performed with a semiconductor laser of 3 mW at 650 nm, and fluorescence was measured. As a result, the detection sensitivity was $2.1 \times 10^{-4}$ (mg/ml). Also, the output-power of the semiconductive laser was elevated to 30 mW, but the measurement was not possible due to background interference.

INDUSTRIAL APPLICABILITY

As described above, since the apparatus for the fluoroimmunoassay of the present invention prevents the reflection of the excitation light at the sensing portion, it is not necessary to form a reflector at the tip end of the optical fiber at the sensing portion as in the prior art. Also, since there is no reflection of the excitation light, there is no mixing of the excitation light with fluorescence, and the load on the filter for removing excitation light can be reduced when the output-power of the light source is increased. Also, since it is also possible to omit the filter, the loss of fluorescence at the filter can be reduced and high sensitivity can be achieved. Also, in the present invention, since it is not necessary to remove the excitation light or to correct the data from the detector, the size reduction of the entire apparatus is possible.

We claim:

1. An apparatus for performing a competitive or sandwich fluoroimmunoassay for an analyte in a test sample wherein said sample is contacted with (a) an optical fiber having an end surface comprising an antigen or antibody capable of specifically binding to said analyte, and (b) a fluorescence-labeled specific binding partner selected from the group consisting of said analyte and an antigen or antibody capable of specifically binding to said analyte, said apparatus comprising:

(a) an excitation light source,
(b) a fluorescence detector,
(c) an optical fiber comprising (1) an incoming end surface for receiving excitation light from said excitation light source, and
(2) said outgoing end surface having said antigen or antibody immobilized thereon, and
(d) a spectroscope;
wherein said spectroscope is constructed so that it transmits said excitation light to said incoming end surface of said optical fiber and transmits any reflected fluorescence due to bound said fluorescence-labeled specific binding partner from said incoming end surface of said optical fiber to said fluorescence detector; and
wherein said optical fiber
(i) has an angle $\theta$ which defines an angle formed between said outgoing end surface and an incident direction of propagation of said excitation light, and is defined as $$\theta > (\pi/2) - \sin^{-1}(n2/n1)$$

wherein n1 is the refractive index of a core portion of said optical fiber and n2 is the refractive index of a test medium in contact with said optical fiber; and
(ii) has a surface roughness Rmax of 0.005 μm to 5 μm, whereby reflection of said excitation light is prevented.

2. The apparatus according to claim 1, wherein the excitation light source is a semiconductor laser.

3. The apparatus according to claim 1, wherein:
the optical fiber is a plastic optical fiber, said core portion of the fiber is plastic, and the plastic fiber comprises in addition to said core portion a plastic cladding.

4. The apparatus according to claim 1, wherein the spectroscope comprises a pair of prisms having a dielectric multilayer, or a dielectric multilayer film mirror.

5. The apparatus according to claim 4, wherein the dielectric multilayer film mirror is a dielectric multilayer film mirror having a wavelength selectivity or a dielectric multilayer film mirror having a polarization plane selectivity.

6. A sensing chip for performing a competitive or sandwich fluoroimmunoassay for an analyte in a test sample wherein said sample is contacted with (a) an optical fiber having an end surface comprising an antigen or antibody capable of specifically binding to said analyte, and (b) a fluorescence-labelled specific binding partner selected from the group consisting of said analyte and an antigen or antibody capable of specifically binding to said analyte, said sensing chip being a removable piece of connectable optical fiber comprising:
(1) an incoming end surface which is connectable to a fiber optic for receiving excitation light from an excitation light source, and
(2) said outgoing end surface having said antigen or antibody immobilized thereon; and
wherein said optical fiber of said sensing chip possesses:
(i) an angle $\theta$ which defines an angle formed between said outgoing end surface and an incident direction of propagation of said excitation light, and is defined as $$\theta > (\pi/2) - \sin^{-1}(n2/n1)$$

wherein n1 is the refractive index of a core portion of said optical fiber of said sensing chip and n2 is the refractive index of a test medium in contact with said optical fiber of said sensing chip, and
(ii) a surface roughness Rmax of 0.005 μm to 5 μm, whereby reflection of said excitation light is prevented.

7. The sensing chip according to claim 6, wherein:
the optical fiber of the sensing chip is a plastic optical fiber, said core portion of the fiber is plastic, and the plastic fiber comprises in addition to said core portion a plastic cladding.

* * * * *